United States Patent [19]
Corley et al.

[11] Patent Number: 6,040,319
[45] Date of Patent: Mar. 21, 2000

[54] PROCESS FOR SYNTHESIZING COX-2 INHIBITORS

[75] Inventors: Edward G. Corley, Old Bridge; Ian W. Davies, Princeton; Robert D. Larsen, Bridgewater; Philip J. Pye, Guttenberg; Kai Rossen, Westfield, all of N.J.

[73] Assignee: Merck & Co., Inc., Rahway, N.J.

[21] Appl. No.: 09/298,127

[22] Filed: Apr. 23, 1999

Related U.S. Application Data

[60] Provisional application No. 60/082,888, Apr. 24, 1998, and provisional application No. 60/085,668, May 15, 1998.

[51] Int. Cl.[7] .................. A01N 43/40; C07D 211/30; C07D 211/78; C07D 211/72; C07D 213/62
[52] U.S. Cl. .................. 514/334; 546/257; 546/286; 546/290; 546/300; 514/333; 514/277; 514/344
[58] Field of Search .................. 546/257, 286, 546/290, 300; 514/334, 333, 344, 277

[56] References Cited

U.S. PATENT DOCUMENTS 5,861,419  1/1999  Dube et al. .................. 514/334

OTHER PUBLICATIONS

Die Pharmazie, vol. 51, K. Gorlitzer et al, Darstellung und Reaktionen von 3'-aza-nifedipin. pp. 207–212, Apr. 19, 1996.

*Primary Examiner*—John Kight
*Assistant Examiner*—Rita Desai
*Attorney, Agent, or Firm*—Richard C. Billups; David L. Rose

[57] ABSTRACT

The invention encompasses a process for making compounds of Formula I useful in the treatment of cyclooxygenase-2 mediated diseases.

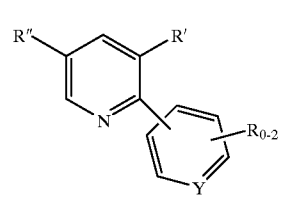

21 Claims, No Drawings

PROCESS FOR SYNTHESIZING COX-2 INHIBITORS

CROSS REFERENCE TO RELATED APPLICATIONS

This application is a non-provisional application based upon U.S. Provisional Applications Ser, No. 60/082,888, filed on Apr. 24, 1998 and Ser. No. 60/085,668, filed on May 15, 1998 priority of which is claimed hereunder.

BACKGROUND OF THE INVENTION

The present invention relates to a process for synthesizing certain COX-2 inhibiting compounds. Additionally certain intermediate compounds are included.

Cyclooxygenase-2 (COX-2) is an enzyme that is implicated in pain, inflammation, hormone-induced uterine contrations and certain types of cancer growth. Until recently, only one form of cyclooxygenase had been characterized, this corresponding to cyclooxygenase-1 or the constitutive enzyme, as originally identified in bovine seminal vesicles. Recently the gene for a second inducible form of cyclooxygenase (cyclooxygenase-2) has been cloned, sequenced and characterized from chicken, murine and human sources. This enzyme is distinct from the cyclooxygenase-1. COX-2, is rapidly and readily inducible by a number of agents including mitogens, endotoxin, hormones, cytokines and growth factors. While the constitutive enzyme, cyclooxygenase-1, is responsible, in large part, for endogenous basal release of prostaglandins and hence is important in their physiological functions such as the maintenance of gastrointestinal integrity and renal blood flow, the inducible form, cyclooxygenase-2, is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will reduce fever, inhibit the inflammatory process, counteract hormone-induced uterine contractions and have potential anti-cancer effects, along with a diminished ability to induce some of the mechanism-based side effects.

One object of the present invention is to provide a synthesis scheme for COX-2 inhibiting compounds which utilizes reduced temperatures in the synthesis.

Another object of the present invention is to utilize a synthetic route that provides high yields.

Another object of the present invention is to provide a synthesis scheme that utilizes a minimum of process steps.

These and other objects will be apparent to those of ordinary skill from the teachings contained herein.

SUMMARY OF THE INVENTION

A process for synthesizing a compound of the formula I:

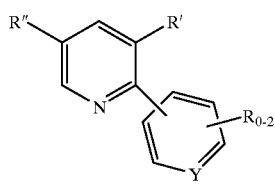

is disclosed wherein:
0-2 R groups are present;
each R, R' and R" independently represents $C_{1-10}$alkyl, $C_{6-10}$aryl, aralkyl, halo, —S(O)$_m$H, —S(O)$_m$C$_{1-6}$alkyl, —S(O)$_m$aryl, nitro, amino, $C_{1-6}$alkylamino, di-$C_{1-6}$alkylamino, —S(O)$_m$NH$_2$, —S(O)$_m$NHC$_{1-6}$alkyl, —S(O)$_m$NHC(O)CF$_3$ and cyano, the alkyl and aryl groups, and the alkyl and aryl portions of aralkyl, —S(O)$_m$C$_{1-6}$alkyl, —S(O)$_m$aryl, $C_{1-6}$alkylamino, di-$C_{1-6}$alkylamino and —S(O)$_m$NHC$_{1-6}$alkyl being optionally substituted with 1–3 groups selected from $C_{1-4}$ alkyl, aryl, halo, hydroxyl, —S(O)$_m$H, —S(O)$_m$C$_{1-6}$alkyl, —CN, $C_{1-6}$alkoxy, amino, $C_{1-6}$alkylamino, di-$C_{1-6}$alkylamino, —S(O)$_m$NH$_2$, —S(O)$_m$NHC$_{1-6}$alkyl, —S(O)$_m$NHC(O)CF$_3$ and aryloxy;

Y is C or N;

and m is 0, 1 or 2, comprising reacting a compound of formula II:

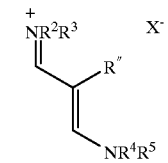

wherein $R^2$ through $R^5$ each independently represent $C_{1-6}$ alkyl, aryl or aralkyl, and X- represents a suitable counterion, with a compound of the formula III:

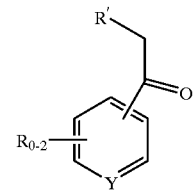

wherein R, R' and Y are as previously defined, in the presence of a base to produce a compound of formula I.

Certain intermediate compounds are also included.

DETAILED DESCRIPTION OF THE INVENTION

The invention is described in detail using the terms defined below unless otherwise specified.

The term "alkyl" refers to a monovalent alkane (hydrocarbon) derived radical containing from 1 to 15 carbon atoms unless otherwise defined. It may be straight, branched or cyclic. Preferred straight or branched alkyl groups include methyl, ethyl, propyl, isopropyl, butyl and t-butyl. Preferred cycloalkyl groups include cyclopentyl and cyclohexyl.

Alkyl also includes a straight or branched alkyl group which contains or is interrupted by a cycloalkylene portion. Examples include the following:

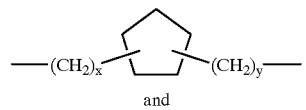

and

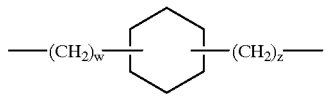

wherein: x plus y=from 0–10 and w plus z=from 0–9.

The alkylene and monovalent alkyl portion(s) of the alkyl group can be attached at any available point of attachment to the cycloalkylene portion.

When substituted alkyl is present, this refers to a straight, branched or cyclic alkyl group as defined above, substituted with 1–3 groups as defined with respect to each variable.

The term "alkoxy" refers to those groups of the designated length in either a straight or branched configuration. Exemplary of such alkoxy groups are methoxy, ethoxy, propoxy, isopropoxy, butoxy, isobutoxy, t-butoxy, pentoxy, isopentoxy, hexoxy, isohexoxy and the like.

The term "halogen" is intended to include fluorine, chlorine, bromine and iodine.

Aryl refers to aromatic rings e.g., phenyl, substituted phenyl and like groups as well as rings which are fused, e.g., naphthyl. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Preferred substituted aryls include phenyl and naphthyl substituted with one or two groups.

X- represents a suitable counterion. Hence, the intermediates of formula II are salt forms which may or may not be "pharmaceutically acceptable" as defined below. A subset of values of X- which are of particular interest includes the following: phosphates, e.g., hexafluorophosphate and the like; sulfates; sulfonates, e.g., mesylate, tosylate, triflate and the like; acetates, e.g., acetate, trifluoroacetate and the like; perchlorate; borate, e.g., tetrafluoroborate, tetraphenylborate and the like; antimonate, e.g., hexafluoroantimonate; halide, e.g., Cl, F, Br and I; benzoate and napsylate.

Preferred values of X- which is used in the process described herein are selected from the group consisting of: hexafluorophosphate; the halides; sulfate; the sulfonates; trifluoroacetate; perchlorate; tetrafluoroborate; tetraphenylborate and hexafluoroantimonate.

Salts encompassed within the term "pharmaceutically acceptable salts" refer to substantially non-toxic salts of the compounds which are generally prepared by reacting the free base with a suitable organic or inorganic acid. Representative salts include the following:

acetate, benzoate, the halides; napsylate and phosphate/diphosphate.

Preferred values of X- which pertain to the novel intermediates described herein include: hexafluorophosphate, tetrafluoroborate, tetraphenylborate and hexafluoroantimonate.

The compounds used in the present invention may contain one or more asymmetric carbon atoms and may exist in racemic and optically active forms. All of these compounds are useful within the scope of the present invention. When a compound is chiral, the separate enantiomers, substantially free of the other, are included along with mixtures of the enantiomers. Also are polymorphs and hydrates of the compounds.

The compounds of formula I can be administered in oral dosage forms such as tablets, capsules (each including timed release and sustained release formulations), pills, powders, granules, elixirs, tinctures, suspensions, syrups and emulsions. Likewise, they may also be administered parenterally, e.g., by intravenous (both bolus and infusion), intraperitoneal, subcutaneous or intramuscular injection.

The following abbreviations are used:

| | | |
|---|---|---|
| Me | = | methyl |
| Et | = | ethyl |
| n-Pr, Pr | = | normal propyl |
| i-Pr | = | isopropyl |
| n-Bu, Bu | = | normal butyl |
| i-Bu | = | isobutyl |
| s-Bu | = | secondary butyl |
| t-Bu | = | tertiary butyl |
| c-Pr | = | cyclopropyl |
| c-Bu | = | cyclobutyl |
| c-Pen | = | cyclopentyl |
| c-Hex | = | cyclohexyl |
| Bn | | benzyl |
| BOC, Boc | | t-butyloxycarbonyl |
| BOP | | Benzotriazol-1-yloxy tris/dimethylamino)-phosphonium hexafluorophosphate |
| calc. | | calculated |
| CBZ, Cbz | | Benzyloxycarbonyl |
| CDI | | N,N'-carbonyldiimidazole |
| DCC | | Dicyclohexylcarbodiimide |
| DCM | | dichloromethane |
| DIEA | | diisopropylethylamine |
| DMF | | N,N'-dimethylformamide |
| DMAP | | 4-Dimethylaminopyridine |
| DSC | | N,N'-disuccinimidyl carbonate |
| EDC | | 1-(3-dimethylaminopropyl)-3-ethylcarbodiimide hydrochloride |
| EI-MS | | Electron ion-mass spectroscopy |
| EtOAc | | ethyl acetate |
| EtOH | | ethanol |
| eq. | | equivalent(s) |
| FAB-MS | | Fast atom bombardment-mass spectroscopy |
| HMDS | | bis(trimethylsilyl)amide |
| HOAc | | acetic acid |
| HOBT, HOBt | | Hydroxybenztriazole |
| HPLC | | High pressure liquid chromatography |
| KHMDS | | Potassium bis(trimethylsilyl)amide |
| LAH | | Lithium aluminum hydride |
| LDA | | lithium diethylamide |
| LHMDS | | Lithium bis(trimethylsilyl)amide |
| MeOH | | methanol |
| MF | | Molecular formula |
| MHz | | Megahertz |
| MPLC | | Medium pressure liquid chromatography |
| NMM | | N-Methylmorpholine |
| NMR | | Nuclear Magnetic Resonance |
| Ph | | phenyl |
| prep. | | prepared |
| TFA | | Trifluoroacetic acid |
| THF | | Tetrahydrofuran |
| TLC | | Thin layer chromatography |
| TMS | | Trimethylsilane |

In one aspect of the invention, a process for synthesizing a compound of the formula I:

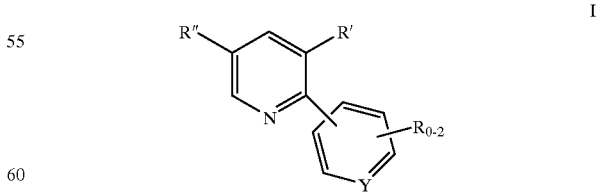

is disclosed wherein:
0-2 R groups are present;
each R, R' and R" independently represents $C_{1-10}$alkyl, $C_{6-10}$aryl, aralkyl, halo, $-S(O)_mH$, $-S(O)_mC_{1-6}$alkyl, $-S(O)_m$aryl, nitro, amino, $C_{1-6}$alkylamino, di-$C_{1-6}$ alkylamino, —S(O)$_m$NH$_2$, —S(O)$_m$NHC$_{1-6}$alkyl, —S(O)$_m$NHC(O)CF$_3$ and cyano, the alkyl and aryl groups, and the alkyl and aryl portions of aralkyl, —S(O)$_m$C$_{1-6}$alkyl, —S(O)$_m$aryl, C$_{1-6}$alkylamino, di-C$_{1-6}$alkylamino and —S(O)$_m$NHC$_{1-6}$alkyl being optionally substituted with 1–3 groups selected from C$_{1-4}$ alkyl, aryl, halo, hydroxyl, —S(O)$_m$H, —S(O)$_m$C$_{1-6}$alkyl, —CN, C$_{1-6}$alkoxy, amino, C$_{1-6}$alkylamino, di-C$_{1-6}$alkylamino, —S(O)$_m$NH$_2$, —S(O)$_m$NHC$_{1-6}$alkyl, —S(O)$_m$NHC(O)CF$_3$ and aryloxy;

Y is C or N;

and m is 0, 1 or 2, comprising reacting a compound of formula II:

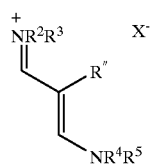

II wherein R$^2$ through R$^5$ each independently represent C$_{1-6}$ alkyl, aryl or aralkyl, and X- represents a suitable counterion, with a compound of the formula III:

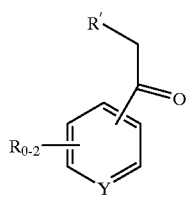

III wherein R, R' and Y are as previously defined, in the presence of a base to produce a compound of formula I.

In a preferred aspect of the invention, a process for synthesizing a compound of the formula I':

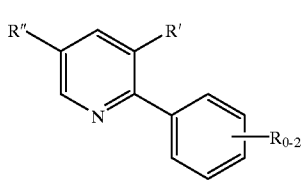

I' is disclosed wherein:

0–2 R groups are present;

each R, R' and R" independently represents C$_{1-10}$alkyl, C$_{6-10}$aryl, aralkyl, halo, —S(O)$_m$H, —S(O)$_m$C$_{1-6}$alkyl, —S(O)$_m$aryl, nitro, amino, C$_{1-6}$alkylamino, di-C$_{1-6}$alkylamino, —S(O)$_m$NH$_2$, —S(O)$_m$NHC$_{1-6}$alkyl, —S(O)$_m$NHC(O)CF$_3$ and cyano, the alkyl and aryl groups, and the alkyl and aryl portions of aralkyl, —S(O)$_m$C$_{1-6}$alkyl, —S(O)$_m$aryl, C$_{1-6}$alkylamino, di-C$_{1-6}$alkylamino and —S(O)$_m$NHC$_{1-6}$alkyl being optionally substituted with 1–3 groups selected from C$_{1-4}$ alkyl, aryl, halo, hydroxyl, —S(O)$_m$H, —S(O)$_m$C$_{1-6}$alkyl, —CN, C$_{1-6}$alkoxy, amino, C$_{1-6}$alkylamino, di-C$_{1-6}$alkylamino, —S(O)$_m$NH$_2$, —S(O)$_m$NHC$_{1-6}$alkyl, —S(O)$_m$NHC(O)CF$_3$ and aryloxy;

Y is C or N;

and m is 0, 1 or 2, comprising reacting a compound of formula II:

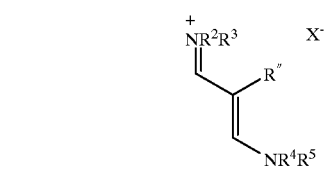

II wherein R$^2$ through R$^5$ each independently represent C$_{1-6}$ alkyl, aryl or aralkyl, and X- represents a suitable counterion, with a compound of the formula III:

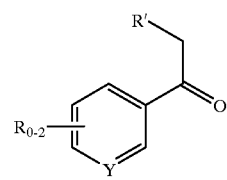

III' wherein R, R' and Y are as previously defined, in the presence of a base to produce a compound of formula I'.

An aspect of the invention that is of particular interest relates to the processes described above, wherein one R group is present and is C$_{1-10}$alkyl, C$_{6-10}$aryl, aralkyl, halo, —S(O)$_m$H, —S(O)$_m$C$_{1-6}$alkyl, —S(O)$_m$aralkyl, —S(O)$_m$aryl, nitro or cyano.

More particularly, the processes that are of particular interest relates to the process described above wherein one R is present and represents a C$_{1-10}$ alkyl group. Even more particularly, the process relates to the process described above wherein one R is present which represents methyl. Most preferred is the process that is described above wherein one R is present and represents methyl attached as follows:

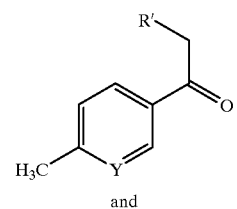

III'-1 and

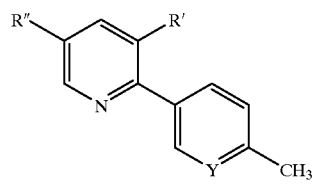

I'-1

Within this subset, all other variables are as originally defined.

In another aspect, the invention encompasses a process for making a compound of formula I wherein Y represents N. Within this subset, all other variables are as originally defined.

In another aspect of the invention that is of particular interest, the process encompasses a compound wherein R' is selected from the group consisting of: $C_{6-10}$ aryl substituted with $-S(O)_mC_{1-6}$ alkyl. More particularly, the process encompasses a compound wherein R' represents phenyl substituted with methanesufonyl at the 4' position as shown below:

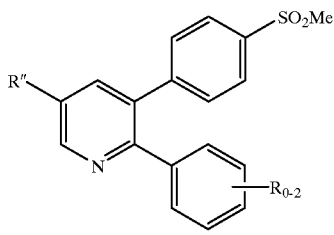

Within this subset, all other variables are as originally defined.

In another aspect of the invention that is of particular interest, the process encompasses a compound wherein R" is selected from $C_{1-10}$ alkyl, $C_{6-10}$ aryl, aralkyl, halo, $-S(O)_m$H, $-S(O)_mC_{1-6}$ alkyl, nitro and cyano. More particularly, the invention that is of interest relates to a process wherein R" is halo or $C_{6-10}$ aryl. Even more particularly, R" represents halo, especially chloro. Within this subset, all other variables are as originally defined.

In another aspect of the invention, the process utilizes a compound of formula II wherein $R^2$ through $R^5$ represent $C_{1-6}$ alkyl, and in particular, methyl. Within this subset, all other variables are as originally defined.

In another aspect of the invention, the process utilizes a compound of formula II wherein X- represents a member selected from the group consisting of: hexafluorophosphate, halide, sulfate, sulfonate, borate, trifluoroacetate or perchlorate. More particularly, X- represents a member selected from the group consisting of: hexafluorophosphate, chloride, a sulfonate selected from methanesulfonate, toluenesulfonate and trifluoromethylsulfonate, tetrafluoroborate or trifluoroacetate. Within this subset, all other variables are as originally defined.

As used herein, the term "base" refers to organic and inorganic bases, such as sodium or potassium hydroxide, cesium carbonate, Li, Na or K alkoxide bases, such as sodium, potassium or lithium isopropoxide, sodium, potassium or lithium t-butoxide and the like, Li, Na or K amide bases, such as LHMDS, LDA and the like, and Na, K or Li hydride bases.

For purposes of this specification, the reactions, unless otherwise specified, are generally carried out in a solvent such as benzene, chlorobenzene, dichlorobenzene, toluene and xylene; etheral solvents such as diethyl ether, di-n-butyl and diisopentyl ethers, anisole, cyclic ethers such as tetrahydropyran, 4-methyl-1,3-dioxane, dihydropyran, tetrahydrofurfuryl, methyl ether, ethyl ether, 2-ethoxytetrahydrofuran and tetrahydrofuran (THF); halocarbon solvents including mono or dihalo $C_{1-4}$ alkyl such as dichloromethane; $C_{6-10}$ linear, branched or cyclic hydrocarbon solvents including hexane; and nitrogen containing solvents including N,N-dimethylacetamide, N,N-dimethylformamide (DMF), N-ethylpyrrolidinone, N-methylpyrrolidinone, and acetonitrile. Preferable solvents are alcohol, THF and DMF.

Typically the reaction is conducted in a substantially non-reactive solvent, e.g., tetrahydrofuran, dioxane, $C_{1-6}$alkanol, chlorobenzene, dichlorobenze or xylene.

The reaction can surprisingly be conducted at substantially room temperatures.

The compounds of formula I are useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compounds of formula I may also be useful for the treatment of dementia including pre-senile and senile dementia, and in particular, dementia associated with Alzheimer Disease (ie Alzheimer's dementia).

By virtue of its high cyclooxygenase-2 (COX-2) activity and/or its selectivity for cyclooxygenase-2 over cyclooxygenase-1 (COX-1), compounds of formula I are useful as an alternative to other non-steroidal antiinflammatory drugs (NSAID'S) particularly where such non-steroidal antiinflammatory drugs may be contraindicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems (including those relating to reduced or impaired platelet function); kidney disease (eg impaired renal function); those prior to surgery or taking anticoagulants; and those susceptable to NSAID induced asthma.

The compounds are inhibitors of cyclooxygenase-2 and are thereby useful in the treatment of cyclooxygenase-2 mediated diseases as enumerated above. This activity is illustrated by their ability to selectively inhibit cyclooxygenase-2 over cyclooxygenase-1. Accordingly, in one assay, the ability of the compounds of this invention to treat cyclooxygenase mediated diseases can be demonstrated by measuring the amount of prostaglandin $E_2$ ($PGE_2$) synthesized in the presence of arachidonic acid, cyclooxygenase-1 or cyclooxygenase-2 and a compound of formula I. The $IC_{50}$ values represent the concentration of inhibitor required to return $PGE_2$ synthesis to 50% of that obtained as compared to the uninhibited control.

For the treatment of any of these cyclooxygenase mediated diseases, compounds of formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

The process is further described in connection with the following scheme.

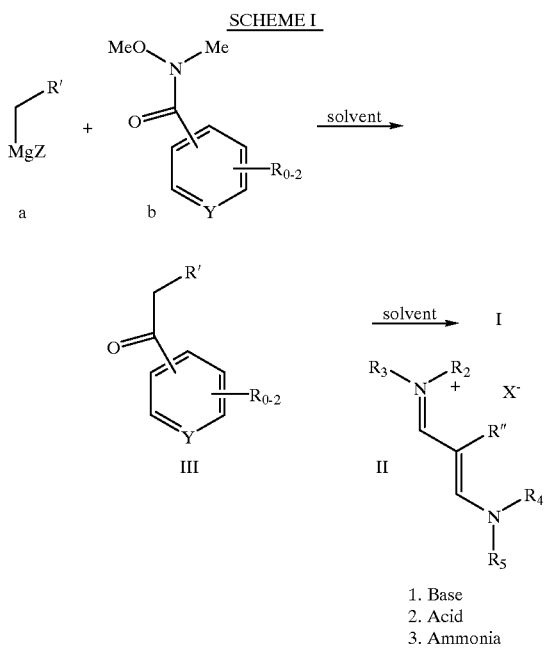

SCHEME I

1. Base
2. Acid
3. Ammonia

The process described herein can be described in connection with the generic description above. Grignard reagent a (0.1–3 M, 0.8–2 equivalents) is prepared from the corresponding halide, e.g., Z equals chloride, and magnesium in a suitable solvent, such as THF, ether, toluene or mixtures thereof. The Grignard reagent is added to a cold solution (0 to −78° C., preferrably −10 to −30° C.) of amide b in a suitable solvent, leading to the formation of ketone III. The ketone III is isolated after aquous workup by extraction and crystallization.

Treatment of ketone III (0.0514 2 M) with a suitable base, e.g., a metal alkoxide, in a suitable solvent at about −78° C. to about 50° C., typically less than about 20° C., results in the formation of an enolate intermediate (not shown). The enolate is reacted with the trimethinium salt to form an intermediate (not shown) which is quenched into a suitable acid (0.05–10 M). An example is acetic acid.

Ammonia is added to the mixture (typically as an aqueous solution) and the mixture is aged at ambient to reflux temperature) for several hours. The product is isolated by extraction using, e.g., ether, ethyl acetate or methylene chloride and crystallization to form a compound of formula I.

The invention is further illustrated by the following non-limiting examples in which, unless stated otherwise:
(i) all operations were carried out at room or ambient temperature, that is, at a temperature in the range of about 18–25° C.; evaporation of solvent was carried out under reduced pressure (600–4000 pascals: 4.5–30 mm. Hg) with a bath temperature of up to about 60° C.; the course of reactions was followed by thin layer chromatography (TLC) or High Pressure Liquid Chromatography (HPLC) and reaction times are given for illustration only; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; when given, NMR data is in the form of delta (d) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

PREPARATIVE EXAMPLE 1

Weinreb

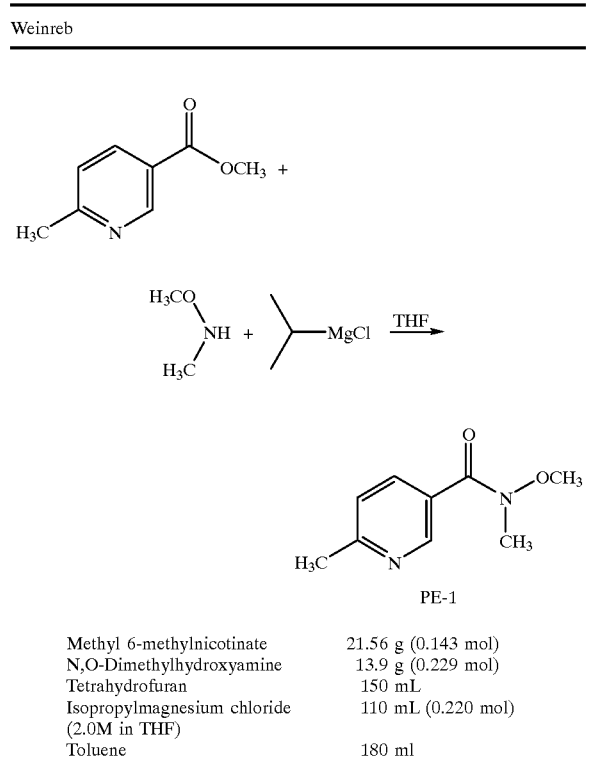

| | |
|---|---|
| Methyl 6-methylnicotinate | 21.56 g (0.143 mol) |
| N,O-Dimethylhydroxyamine | 13.9 g (0.229 mol) |
| Tetrahydrofuran | 150 mL |
| Isopropylmagnesium chloride (2.0M in THF) | 110 mL (0.220 mol) |
| Toluene | 180 ml |

A solution of methyl 6-methylnicotinate (21.56 g), and N,O-dimethylhydroxylamine (13.9 g) in THF (150 mL) was cooled to −10° C. Isopropylmagnesium chloride (110 mL) was added over 2.5 h. The reaction mixture was poured into aqueous acetic acid (10 vol %, 126 mL) at 5° C. Toluene (60 mL) was added to the mixture, then the layers were separated. The aqueous layer was extracted with toluene (2×60 mL) and the solvent removed. Solid impurities were removed by filtration and the filtrate was concentrated to afford the Weinreb amide PE-1 as a light orange oil (24.2 g).

PREPARATIVE EXAMPLE 2

Grignard

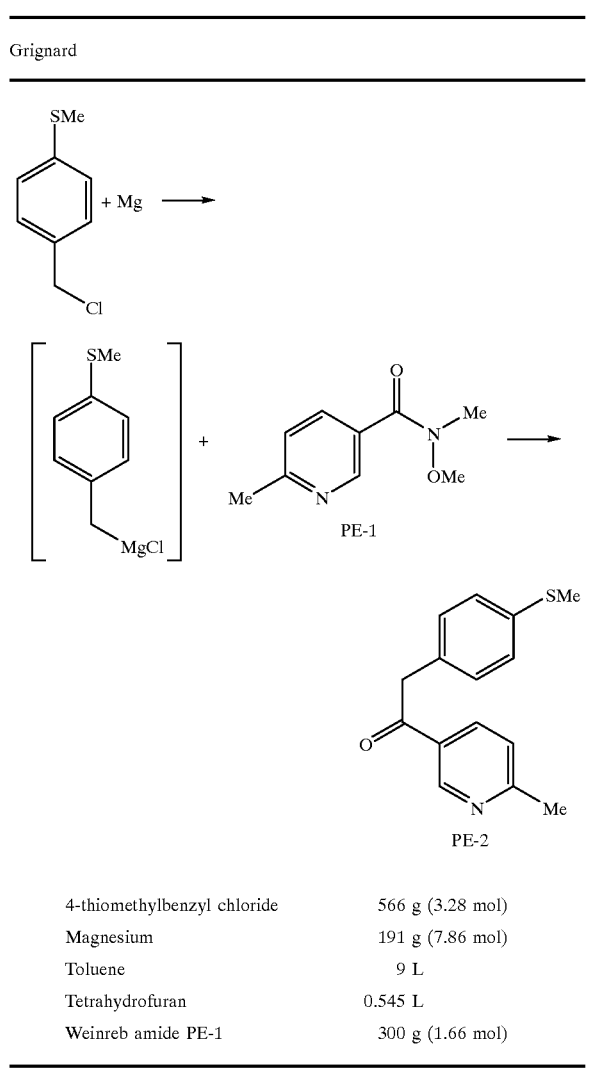

| 4-thiomethylbenzyl chloride | 566 g (3.28 mol) |
| --- | --- |
| Magnesium | 191 g (7.86 mol) |
| Toluene | 9 L |
| Tetrahydrofuran | 0.545 L |
| Weinreb amide PE-1 | 300 g (1.66 mol) |

A mixture of magnesium (191 g, 7.86 mol) toluene (4 L), 4-thiomethylbenzyl chloride (566 g, 3.28 mol) and tetrahydrofuran (0.545 L, 6.73 mol) were charged over 3–4 hours. An additional flask was charged with Weinreb amide PE-1 (300 g, 1.66 mol) and toluene (1.7 L) and cooled to −20° C. The Grignard solution prepared above was added over 30 minutes and the mixture was aged for 1 hour. The reaction mixture was quenched by the addition of 50% aqueous acetic acid (0.5 L). Toluene (1 L) and water (1 L) were added and the layers were separated. The aqueous layer was extracted with toluene (2×2 L). The combined organic extracts were extracted with dilute hydrochloric acid (1×2 L). Ethyl acetate was added to the aqueous layer and the pH was adjusted with ammonia (0.6 L). The phases were separated and the aqueous layer was extracted with ethyl acetate (2×1.25 L). The combined extracts were concentrated on a rotary evaporator to give PE-2 as a light yellow solid (326.5 g).

PREPARATIVE EXAMPLE 3

Oxidation

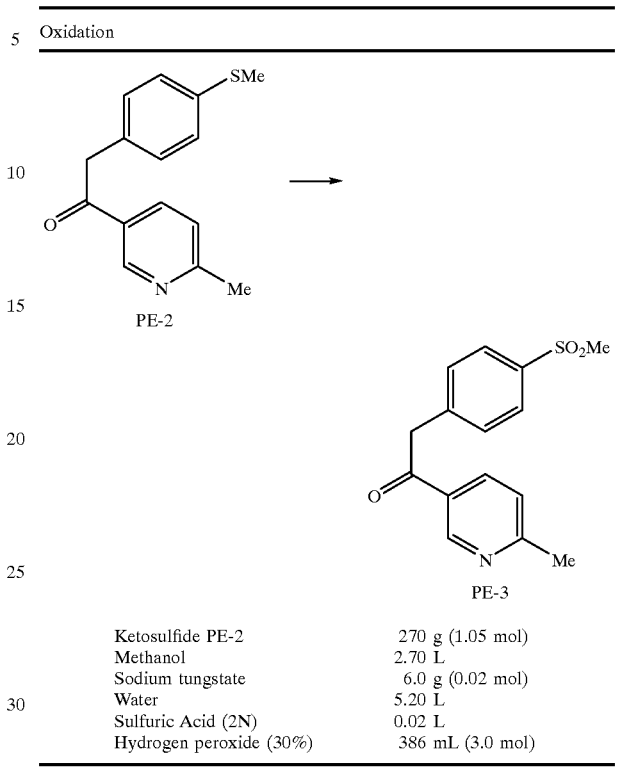

| Ketosulfide PE-2 | 270 g (1.05 mol) |
| --- | --- |
| Methanol | 2.70 L |
| Sodium tungstate | 6.0 g (0.02 mol) |
| Water | 5.20 L |
| Sulfuric Acid (2N) | 0.02 L |
| Hydrogen peroxide (30%) | 386 mL (3.0 mol) |

A mixture of ketosulfide PE-2 (270 g, 1.05 mol), sulfuric acid (2N) (20 mL), and methanol (2.70 L) was heated at 55° C. An aqueous solution of sodium tungstate (6.0 g, 0.02 mol) was added, then hydrogen peroxide (380 mL) was added over 1 hour. Water (3 L) was added and the mixture was cooled to ambient temperature, then filtered. The solids were washed with water (2 L) and dried under vacuum with a stream of nitrogen to give the ketosulfone PE-3 (250.2 g) as a colorless solid.

EXAMPLE 1

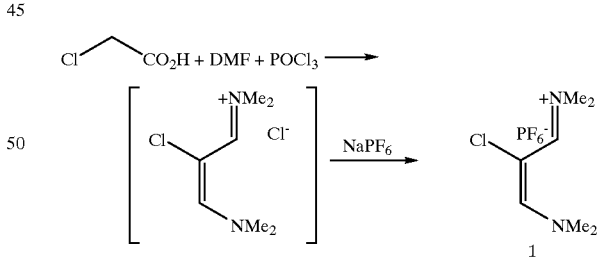

Chloroacetic acid (0.99 kg, 10.57 mmol) was added to dimethylformamide (4.37 kg, 59.78 mol) and the mixture was heated to 75° C. Phosphorus oxychloride (3.36 Kg, 21.91 mol) was added over 5 hrs. The reaction mixture is aged for 3 hrs, then cooled to ambient temperature. The reaction mixture and sodium hydroxide (19.7 kg) were added concurrently over 2 hrs. to a mixture of water (12 kg), 60% by weight aqueous hexafluorophosphoric acid(2.87 kg, 11.71 mol) and 4.7 N sodium hydroxide(2.3 kg) at <9° C. The reaction flask was washed with dimethylformamide (0.36 kg) and added to the quench. The mixture was aged for 40 min. then filtered. The crude solid was washed with water (8.6 kg). The solid was recrystallized from water (10.8 kg) and isopropanol (3.8 kg) by heating to 67° C. The mixture was cooled to 4° C. then filtered. The solid was washed with water/isopropanol (11 kg, 26:1) and dried to give the target compound 1 as a yellow solid (2.28 kg).

EXAMPLE 2

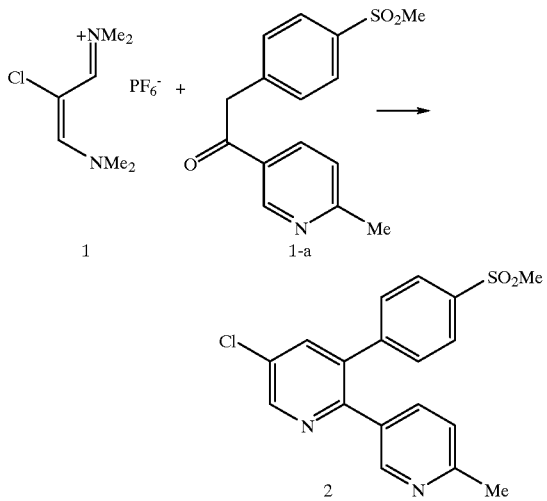

To a suspension of compound 1-a (1.5 kg, 5.12 mol) in THF (10 L) was added potassium butoxide (617 g, 5.5 mol) in THF (5.38 L, 5.38 mol) at <15° C. Compound 1 (1.65 kg,. 4.6 mol) was added and the reaction mixture was aged at ambient temperature. The reaction mixture was transferred to a solution of acetic acid (2.0 L) in THF (5 L) and the mixture was stirred for 1 hr. Concentrated aqueous ammonium hydroxide (4 L) was added and the mixture was heated at reflux for 3 hrs. The mixture was cooled to 22° C. and the layers were separated. The organic layer was concentrated to 3 L and isopropyl acetate (5 L) was added. The resulting solution was again concentrated to 34 L and isopropyl acetate (19 L) was added. The solution was washed with saturated sodium bicarbonate (2×9.5 L) and water (2×9.5 L), concentrated to dryness and purified to provide compound 2 as a solid (1.65 kg).

EXAMPLE 3

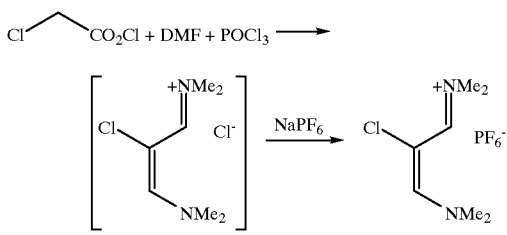

Chloroacetyl chloride (14.50 g, 0.112 mol) was added to dimethylformamide (50 mL) and the mixture was heated to 75° C. to give a clear yellow solution. Phosphorus oxychloride (18.9 g, 0.123 mol) was added at 5 mL/h. The reaction mixture is aged for 3 h then cooled to ambient temperature. The reaction mixture and 5N sodium hydroxide (70 mL) were added concurrently over 1 hr to a mixture of water (200 mL) and sodium hexafluorophosphate (21 g, 0.125 mol) at <9° C. The reaction flask was washed with dimethylformamide (2 mL) and added to the quench. The mixture was aged for 40 minutes then filtered.

The crude solid was washed with water (100 mL). The solid was recystallized from water (224 mL) and isopropanol (56 mL) by heating to 70° C. The mixture was cooled to 4° C. then filtered. The solid was washed with water/isopropanol (100 mL, 20:1) and dried to give CDT-phospahte as a light yellow solid (26.8 g).

What is claimed is:

1. A process for synthesizing a compound of the formula I:

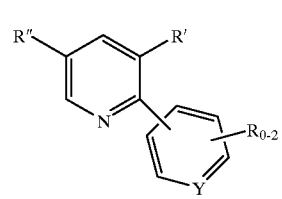

wherein:

0-2 R groups are present;

each R, R' and R" independently represents $C_{1-10}$alkyl, $C_{6-10}$aryl, aralkyl, halo, —$S(O)_mH$, —$S(O)_mC_{1-6}$alkyl, —$S(O)_m$aryl, nitro, amino, $C_{1-6}$alkylamino, di-$C_{1-6}$alkylamino, —$S(O)_mNH_2$, —$S(O)_mNHC_{1-6}$alkyl, —$S(O)_mNHC(O)CF_3$ and cyano, the alkyl and aryl groups, and the alkyl and aryl portions of aralkyl, —$S(O)_mC_{1-6}$alkyl, —$S(O)_m$aryl, $C_{1-6}$alkylamino, di-$C_{1-6}$alkylamino and —$S(O)_mNHC_{1-6}$alkyl being optionally substituted with 1–3 groups selected from —$S(O)_mC_{1-6}$alkyl, —CN, $C_{1-6}$alkoxy, amino, $C_{1-6}$alkylamino, di-$C_{1-6}$alkylamino, —$S(O)_mNH_2$, —$S(O)_mNHC_{1-6}$alkyl, —$S(O)_mNHC(O)CF_3$ and aryloxy;

Y is N;

and m is 0, 1 or 2, comprising reacting a compound of formula II:

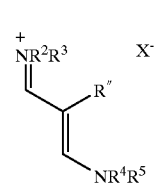

wherein $R^2$ through $R^5$ each independently represent $C_{1-6}$ alkyl, aryl or aralkyl, and X- represents a suitable counterion, with a compound of the formula III:

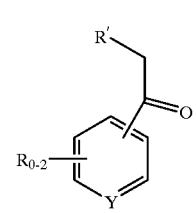

wherein R, R' and Y are as previously defined, in the presence of a base to produce a compound of formula I.

2. A process in accordance with claim 1 wherein a compound of the formula I':

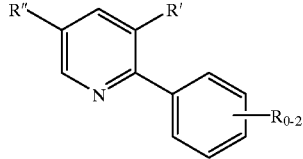

is produced, in which R, R' and R" are as originally defined, comprising reacting a compound of formula II:

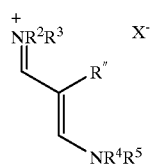

wherein $R^2$ through $R^5$ and X- are as originally defined, with a compound of the formula III':

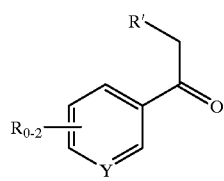

in the presence of a base to produce a compound of formula I'.

3. A process in accordance with claim 1 wherein one R group is present and is $C_{1-10}$ alkyl, $C_{6-10}$ aryl, aralkyl, halo, —S(O)$_m$H, —S(O)$_m$C$_{1-6}$ alkyl, —S(O)$_m$aralkyl, —S(O)$_m$ aryl, nitro or cyano.

4. A process in accordance with claim 3 wherein one R is present and represents $C_{1-10}$ alkyl.

5. A process in accordance with claim 4 wherein one R is present which represents methyl.

6. A process in accordance with claim 2 wherein one R is present and represents methyl attached as follows:

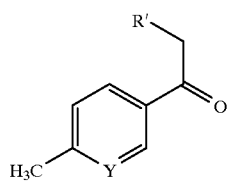

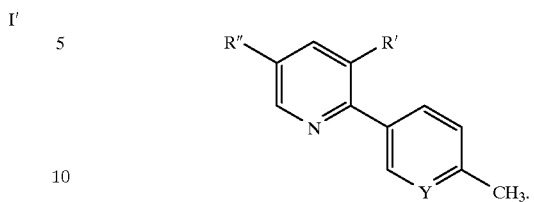

7. A process in accordance with claim 1 wherein R' represents $C_{6-10}$ aryl substituted with —S(O)$_m$C$_{1-6}$ alkyl.

8. A process in accordance with claim 7 wherein R' represents phenyl substituted with methanesufonyl at the 4' position.

9. A process in accordance with claim 1 wherein R" is selected from $C_{1-10}$ alkyl, $C_{6-10}$ aryl, aralkyl, halo, —S(O)$_m$H, —S(O)$_m$C$_{1-6}$ alkyl, nitro and cyano.

10. A process in accordance with claim 9 wherein R" is halo or $C_{6-10}$ aryl.

11. A process in accordance with claim 10 wherein R" represents halo.

12. A process in accordance with claim 11 wherein R" represents chloro.

13. A process in accordance with claim 1 wherein $R^2$ through $R^5$ represent $C_{1-6}$ alkyl.

14. A process in accordance with claim 13 wherein $R^2$ through $R^5$ represent methyl.

15. A process in accordance with claim 1 wherein:

X- represents a member selected from the group consisting of: phosphates; sulfates; acetates; perchlorate; borates; antimonates; halides; benzoate and napsylate.

16. A process in accordance with claim 15 wherein X- represents a member selected from the group consisting of: hexafluorophosphate; sulfate; mesylate; tosylate; triflate; acetate; trifluoroacetate; perchlorate; tetrafluoroborate; tetraphenylborate; hexafluoroantimonate; chloride; bromide; fluoride; iodide; benzoate and napsylate.

17. A process in accordance with claim 16 wherein X- represents hexafluorophosphate.

18. A process in accordance with claim 16 wherein X- represents a halide.

19. A process in accordance with claim 18 wherein the halide is chloride.

20. A process in accordance with claim 1 wherein the base is selected from the group consisting of: Na and K hydroxide; Cs carbonate; Li, Na and K $C_{1-6}$alkoxides; Li, Na and K amides, and Li, Na and K hydrides.

21. A process in accordance with claim 20 wherein the base is selected from the group consisting of: lithium isopropoxide, potassium t-butoxide, LHDMS, NaHMDS, LDA and NaH.

* * * * *

UNITED STATES PATENT AND TRADEMARK OFFICE
CERTIFICATE OF CORRECTION

PATENT NO. : 6,040,319
APPLICATION NO. : 09/298127
DATED : March 21, 2000
INVENTOR(S) : Edward G. Corley et al.

It is certified that error appears in the above-identified patent and that said Letters Patent is hereby corrected as shown below:

Column 5, formula I', reading

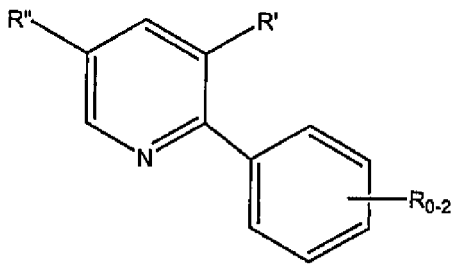   should read   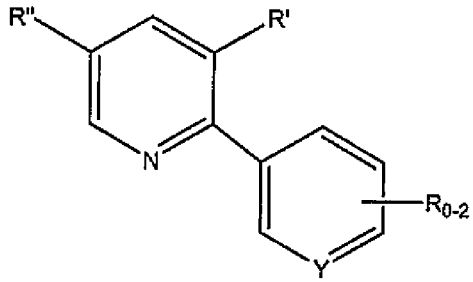

Column 7, formula I'', reading

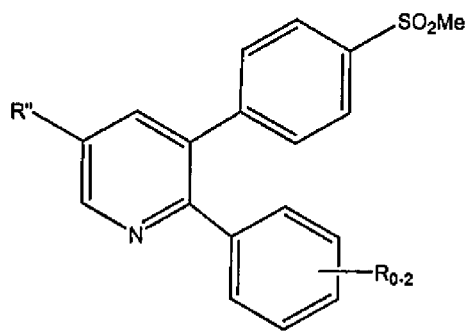   should read   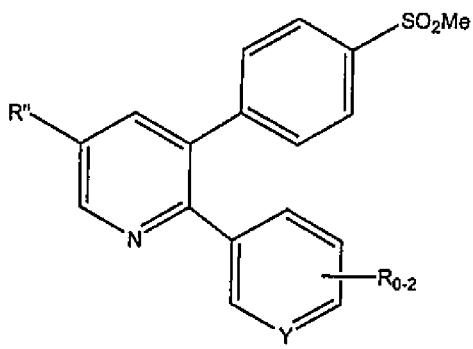

UNITED STATES PATENT AND TRADEMARK OFFICE
CERTIFICATE OF CORRECTION

PATENT NO.       : 6,040,319
APPLICATION NO.  : 09/298127
DATED            : March 21, 2000
INVENTOR(S)      : Edward G. Corley et al.

It is certified that error appears in the above-identified patent and that said Letters Patent is hereby corrected as shown below:

Column 15, formula I', reading

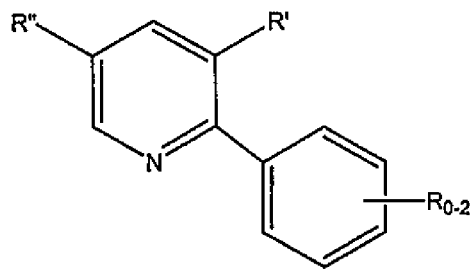  should read  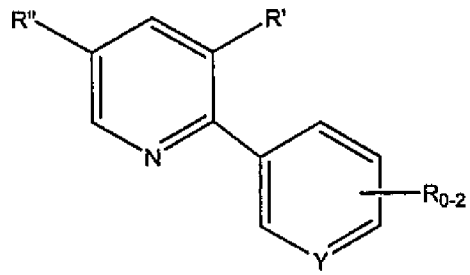

Signed and Sealed this

Twenty-fourth Day of July, 2007

JON W. DUDAS
*Director of the United States Patent and Trademark Office*